United States Patent
Kim

(10) Patent No.: US 10,980,888 B2
(45) Date of Patent: Apr. 20, 2021

(54) SUGAR-BASED SURFACTANT MICROEMULSIONS CONTAINING ESSENTIAL OILS FOR COSMETIC AND PHARMACEUTICAL USE

(75) Inventor: Sanggu Kim, Jurong Island (SG)

(73) Assignee: AGENCY FOR SCIENCE, TECHNOLOGY AND RESEARCH, Singapore (SG)

( * ) Notice: Subject to any disclaimer, the term of this patent is extended or adjusted under 35 U.S.C. 154(b) by 345 days.

(21) Appl. No.: 13/603,335

(22) Filed: Sep. 4, 2012

(65) Prior Publication Data

US 2013/0237613 A1    Sep. 12, 2013

Related U.S. Application Data

(63) Continuation of application No. PCT/SG2007/000284, filed on Aug. 29, 2007.

(51) Int. Cl.

| | | |
|---|---|---|
| *A01N 37/00* | (2006.01) | |
| *A61K 31/215* | (2006.01) | |
| *A01N 37/12* | (2006.01) | |
| *A01N 37/44* | (2006.01) | |
| *A61K 31/24* | (2006.01) | |
| *A01N 25/00* | (2006.01) | |
| *A61K 47/44* | (2017.01) | |
| *A61K 8/60* | (2006.01) | |
| *A61K 8/92* | (2006.01) | |
| *A61K 9/107* | (2006.01) | |
| *A61Q 19/00* | (2006.01) | |
| *A61K 8/06* | (2006.01) | |
| *A61Q 17/00* | (2006.01) | |
| *A61K 8/34* | (2006.01) | |
| *A61K 47/10* | (2017.01) | |
| *A61K 47/36* | (2006.01) | |
| *A61Q 19/08* | (2006.01) | |

(52) U.S. Cl.
CPC ............ *A61K 47/44* (2013.01); *A61K 8/068* (2013.01); *A61K 8/345* (2013.01); *A61K 8/60* (2013.01); *A61K 8/604* (2013.01); *A61K 8/922* (2013.01); *A61K 9/1075* (2013.01); *A61K 47/10* (2013.01); *A61K 47/36* (2013.01); *A61Q 17/005* (2013.01); *A61Q 19/00* (2013.01); *A61Q 19/08* (2013.01)

(58) Field of Classification Search
None
See application file for complete search history.

(56) References Cited

U.S. PATENT DOCUMENTS

| | | | |
|---|---|---|---|
| 5,753,241 A | 5/1998 | Ribier et al. | |
| 5,939,378 A | 8/1999 | Stringer et al. | |
| 6,124,362 A * | 9/2000 | Bradbury | A61K 8/27 514/569 |
| 6,302,969 B2 * | 10/2001 | Moster et al. | 134/40 |
| 2002/0187238 A1 | 12/2002 | Vlad | |
| 2003/0232095 A1 | 12/2003 | Garti et al. | |
| 2007/0087104 A1 | 4/2007 | Chanamai | |
| 2007/0178144 A1 | 8/2007 | Hameyer et al. | |

FOREIGN PATENT DOCUMENTS

| | | |
|---|---|---|
| EP | 1597973 A1 | 11/2005 |
| EP | 1598060 A1 | 11/2005 |
| JP | H01-85906 A | 3/1989 |
| JP | H08-143420 A | 6/1996 |
| JP | 8-206488 | 8/1996 |
| JP | 2000-212066 A | 8/2000 |
| JP | 2004-033820 A | 2/2004 |
| JP | 2005-075817 A | 3/2005 |
| JP | 2005-170859 | 6/2005 |
| JP | 2006-117643 | 5/2006 |
| JP | 2006-182736 A | 7/2006 |
| JP | 2006-249011 A | 9/2006 |
| JP | 2006-273821 | 10/2006 |
| JP | 2007-160287 A | 6/2007 |
| JP | 2010-522871 A | 12/2010 |
| WO | 95/12379 A1 | 5/1995 |
| WO | WO 96/06920 A1 | 3/1996 |
| WO | WO 96/16160 A1 | 5/1996 |
| WO | WO 98/00506 A2 | 1/1998 |
| WO | WO 0222083 A2 * | 3/2002 |
| WO | WO 2004/056332 A1 | 7/2004 |
| WO | 2005/123028 A1 | 12/2005 |
| WO | WO 2007/060171 A1 | 5/2007 |
| WO | WO 2007/060177 A1 | 5/2007 |

OTHER PUBLICATIONS

Garti, et al. ("Improved oil solubilization in oil/water food grade microemulsions in the presence of polyols and ethanol." Journal of agricultural and food chemistry 49.5 (2001): 2552-2562).*
Office Action dated May 26, 2015 for Japanese Application No. JP2010-522871, with English translation, 4 pages.
Japanese Application No. JP2010-522871 , "Final Office Action", dated Dec. 22, 2015, 7 pages.
Somwanshi et al., "Pharmaceutically Use Plasticizers: A Review," World Journal of Biomedical and Pharmaceutical Sciences, 2016, vol. 3, Issue 2, pp. 277-285.

* cited by examiner

*Primary Examiner* — Layla Soroush
(74) *Attorney, Agent, or Firm* — Kilpatrick Townsend & Stockton LLP

(57) ABSTRACT

The present invention relates to a thermodynamically stable, biocompatible, environment friendly, and temperature-insensitive microemulsion containing various botanical essential oils, sugar based surfactants, polyhydric alcohols, and an aqueous phase.

12 Claims, 3 Drawing Sheets

SUGAR-BASED SURFACTANT MICROEMULSIONS CONTAINING ESSENTIAL OILS FOR COSMETIC AND PHARMACEUTICAL USE

CROSS-REFERENCE TO RELATED APPLICATIONS

The present invention is a continuation of PCT/SG2007/000284, filed Aug. 29, 2007. PCT/SG2007/000284 is incorporated in its entirety by reference herein.

TECHNICAL FIELD

The present invention relates to microemulsions containing various essential oils in combination with an aqueous phase and a polyhydric alcohol, stabilized by aid of biocompatible sugar-based surfactant(s) for personal care and pharmaceutical applications.

BACKGROUND OF THE INVENTION

Many personal care and pharmaceutical industries currently provide commercial products to customers in various delivery forms. One typical and popular product is an emulsion such as those in creams, lotions, and gels for topical application. The design of emulsions for cosmetic and pharmaceutical use is quite complex and the crucial drawback of these forms is thermodynamic instability, which causes separation into two immiscible liquid phases (i.e., phase separation). In general, the stability of an emulsion increases with decreasing particle size. In this regard, there is a need for the development of a new and effective delivery system to overcome this drawback.

In recent years, the growing interest in microemulsions has arisen as a powerful alternative to conventional emulsions and as a potential candidate for cosmetic and drug delivery systems. Unlike macroemulsions, microemulsions are optically transparent, thermodynamically stable, possess low viscosity, and are isotropic nanodispersions of oil and aqueous phases stabilized by an interfacial film of surface active molecules. The structure of the microemulsion is classified into three distinct types: (a) water-in-oil microemulsions, in which the aqueous phase is dispersed in the continuous oil phase; (b) bicontinuous microemulsions, in which microdomains of oil and aqueous phases are interdispersed in the system with approximately equal volume; and (c) oil-in-water microemulsions, in which the oil phase is dispersed in the continuous aqueous phase.

Natural essential oils that can be used as potential antioxidant and antimicrobial agents in cosmetic and pharmaceutical use are the growing interest of consumers because of increasing concern about potential side-effects of synthetic additives. Generally, emulsions are used in making lotions, facial toners, shampoos, perfumes and soaps in personal care applications and in pharmaceutical applications for oral or topical use. These benefits are usually achieved by application of the diluted oil to the skin. Most essential oils are used by diluting them with various carrier oils such as soybean oil, sweet almond oil, castor oil, and apricot kernel oil and then applying this blend to the skin for absorption. The research of essential oil-based formulations including the microemulsion delivery system has been extensively studied because of their psychological and physical therapeutic benefits.

U.S. Pat. No. 4,568,480 discloses the preparation of microemulsions containing various fragrance and flavor oils with alkoxylated phenol derivatives that may also contain an additional surfactant. These microemulsions contain 5 to 70 wt %, preferably, 10 to 30 wt %, of the alkoxylated phenol derivative ester, about 0 to 40 wt % of an oil phase, about 30 to 90 wt % water and 0 to 40 wt % of any additional alkoxylated phosphate ester.

U.S. Pat. No. 5,468,725 discloses an alcohol-free transparent perfume formulation containing water, one or more hydrophobic fragrance oils, at least one or more cationic surfactants, a non-ionic surfactant, and amphoteric surfactant with little or no lower alkanols. U.S. Pat. No. 5,707,610 discloses an antibacterial oral hygiene composition comprising sodium benzoate, a weak carboxylic acid, a flavoring agent in combination with anionic surfactants such as sodium dodecyl sulfate and sodium tetradecyl sulfate. U.S. Pat. No. 6,323,171 discloses a multipurpose liquid cleaner in microemulsion form for cleaning and disinfecting hard surfaces which may include 0.1 to 3% by weight of essential oil, perfume, or hydrocarbon ingredient with a mixture of at least one ethoxylated non-ionic surfactant such as Plurafacea® (BASF), Tween® (ICI), and Neodol® (Shell), cationic surfactant as grease removal agent and an amphoteric surfactant as an antibacterial agent in the range of from 0.1 to 20% by weight. U.S. Pat. No. 6,902,756 discloses the preparation of a clear, thermodynamically stable and concentrated oil-in-water microemulsion for the flavoring effect of clear beverages containing at least 30 wt % of flavor oil with at least two non-ionic food grade surfactants having a hydrophilic lipophilic balance (1-ILB) between 9 to 18 such as Tween®, Span®, Glycosperse®, and Polyaldo® series produced by ICI.

The applications of essential oil with prior art formulations have some drawbacks. Due to the relatively high content of the oil phase, the skin feels more sticky and greasy (especially oily skin) and its skin absorption and shelf-life is relatively poor. Also, macroemulsion formulations containing essential oils that are commonly used as cosmetic and drug delivery vehicles are also thermodynamically unstable by mainly coalescence and flocculation. Droplet sizes are much larger, typically 1 to 20 μm range, resulting in a cloudy or milky solution. Obtaining a small particle size is one important issue for more stable and elegant emulsion products. In order to reduce the droplet size to a desired level, special external energy is needed by a high shear mixer or a high pressure homogenizer. The poor solubility of water insoluble or sparingly water soluble cosmetic and pharmaceutical ingredients into aqueous phase solutions is also a crucial technical barrier for cosmetic and pharmaceutical delivery systems. Oil-in-water macroemulsions have been commonly used to obtain a desired concentration in formulations.

Even though microemulsion systems have very good advantages compared to macroemulsions, they still have some problems to solve. M. A. Thevennin et al., "*Sucrose esters/cosurfactant microemulsion systems for transdermal delivery: assessment of bicontinuous structures,*" *International Journal of Pharmaceutics*. 137, 177-186 (1996) describes the performance of sucrose esters to formulate microemulsions containing water and cetearyl octanoate as the oil phase with alkanols as co-surfactant for topical use. High amounts of alkanols as co-surfactant used for the sucrose ester-based microemulsion and relatively narrow microemulsion domain can have some limitations of practical application. The microemulsions described in U.S. Pat. No. 4,568,480 are prepared using a relatively high content of surfactants and co-surfactants sometimes causing allergic reactions on the skin and their physical stabilities may be low at high temperature in the range of 50 to 70° C. The use of conventional anionic surfactants having a strong detergent effect as essential components of microemulsions described in U.S. Pat. Nos. 5,468,725 and 5,707,610 is a critical drawback because of instability and deactivation of other active ingredients including pH-dependent sensitivity. U.S. Pat. Nos. 6,323,171 and 6,902,756 described above employ a complex surfactant system as well as being potentially toxic and unstable and may be harmful to the environment. Microemulsions stabilized by non-ionic surfactants are quite sensitive to temperature because of the decreasing surfactant solubility with increasing temperature, which often shows a phase inversion phenomena. This phase inversion phenomena by non-ionic surfactants can cause some problems for the exploitation of microemulsions as cosmetic and pharmaceutical delivery systems.

In view of the foregoing, what is needed are materials using microemulsion formulations that are biocompatible, non-toxic, and clinically acceptable and the microemulsion itself should be temperature-insensitive at a wide range of temperatures. The current invention satisfies these and other needs.

BRIEF SUMMARY OF THE INVENTION

The present invention provides a microemulsion that has thermodynamic stability, optical transparency and temperature-insensitivity. Advantageously, the microemulsion undergoes spontaneous formation and is simple and easy to prepare and use.

As such, in one embodiment, the present invention provides a microemulsion for a topical application, comprising:
(a) up to 20% w/w of a sugar-based surfactant selected from the group of a sucrose ester, an alkyl polyglucoside and a combination thereof;
(b) up to 10% w/w of a polyhydric alcohol;
(c) up to 10% w/w of an oil selected from the group of an essential oil, a pharmaceutically acceptable oil, and combinations thereof; and
(d) up to 95% w/w water.

In certain aspects, the present invention can further comprise a vitamin such as vitamin A, vitamin E, vitamin K, a derivative thereof or a combination thereof.

In other aspects, the present invention can further comprise an active agent such as an antibacterial, an antibiotic, an antifungal, a retinoid, an insecticide or a combination thereof.

The microemulsions of the present invention have excellent thermodynamic stability that ensure a long shelf-life and are temperature-insensitive over a wide temperature range.

In certain aspects, the present invention is substantially an alkanol-free sugar-based surfactant microemulsion formulation.

In another embodiment, the present invention provides a method for making a microemulsion for a topical application, the method comprising:
(a) admixing a surfactant and optionally a co-surfactant with an essential oil to form an oil phase;
(b) adding the oil phase to water to form a coarse macroemulsion; and
(c) shaking and stirring the coarse macroemulsion to spontaneously form a microemulsion.

In still yet another embodiment, the present invention provides a use of a microemulsion, comprising:
(a) up to 20% w/w of a sugar-based surfactant selected from the group of a sucrose ester, an alkyl polyglucoside and a combination thereof;
(b) up to 10% w/w of a polyhydric alcohol;
(c) up to 10% w/w of an oil selected from the group of an essential oil, a pharmaceutically acceptable oil, and combinations thereof; and
(d) up to 95% w/w water in the manufacture of a medicament for a topical application treatment.

The present invention can be applied for care and cure of skin problems such as skin aging, infection, or disease.

These and other aspects, advantages and embodiments will become more apparent when read with the accompanying figures and detailed description which follow.

DETAILED DESCRIPTION OF THE INVENTION

I. General

Figure 1:
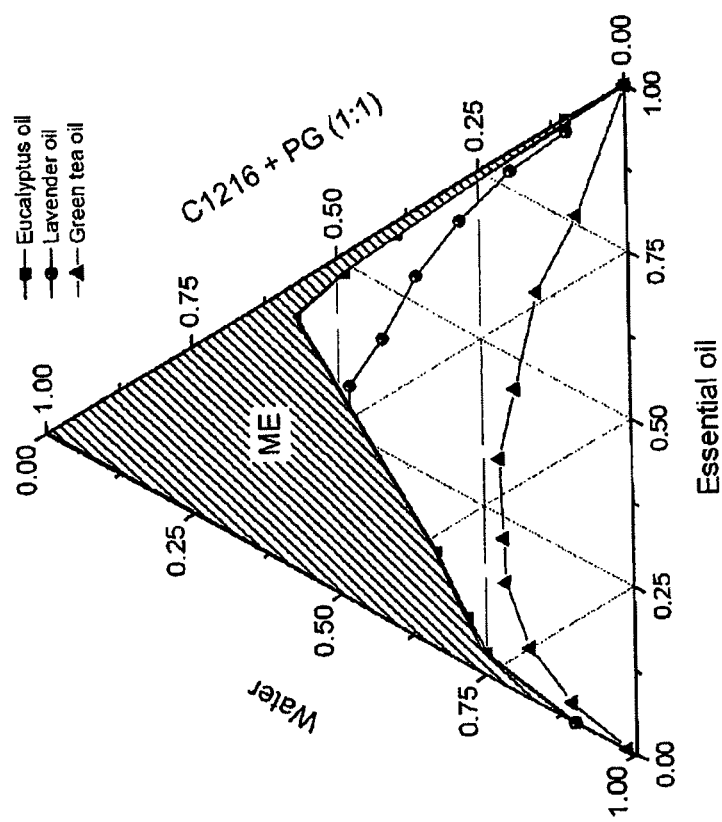
FIG. 1 shows a pseudoternary phase diagram of a microemulsion of the invention illustrating a stable microemulsion domain.

The present invention relates to a biocompatible, thermodynamically stable, and temperature-insensitive microemulsion for topical use in cosmetic and pharmaceutical applications. In certain embodiments, the microemulsions are substantially alkanol-free and have improved skin mildness and reduced skin irritation. Advantageously, the oil-in-water microemulsions are especially useful for water insoluble, or poorly water soluble ingredients such as water-insoluble vitamins. The microemulsions are thermodynamically stable and form spontaneously with gentle shaking and stirring due to a very low interfacial tension. In certain aspects, the average microemulsion droplet diameter is about 10 to 100 nm.

II. Microemulsions

In one embodiment, the present invention provides a microemulsion for a topical application, comprising:
(a) up to 20% w/w of a sugar-based surfactant selected from the group of a sucrose ester, an alkyl polyglucoside and a combination thereof;
(b) up to 10% w/w of a polyhydric alcohol;
(c) up to 10% w/w of an oil selected from the group of an essential oil, a pharmaceutically acceptable oil, and combinations thereof; and
(d) up to 95% w/w water.

The present invention is thermodynamically stable and temperature-insensitive over a wide temperature range (e.g., 5 to 70° C.).

In certain instances, the surfactants as a primary surfactant utilized in the present invention are sucrose fatty acid esters, generally called sucrose esters, which are non-ionic surfactants having sucrose as the hydrophilic group and a fatty acid as the hydrophobic group.

In certain instances, the surface-active agents (also termed "surfactants"), which include sucrose fatty acid esters reside at the interface of the oil and water in the composition, in the form of a microemulsion. A surfactant's hydrophilic/lipophilic balance (HLB) describes the emulsifier's affinity toward water or oil. The HLB scale ranges from 1 (totally lipophilic) to 20 (totally hydrophilic), with 10 representing an equal balance of both characteristics. Lipophilic emulsifiers form water-in-oil (w/o) emulsions; hydrophilic surfactants form oil-in-water (o/w) emulsions. The HLB of a blend of two emulsifiers equals the weight fraction of emulsifier "A" times its HLB value, plus the weight fraction of emulsifier "B" times its HLB value (weighted average). The surface active agent according to the present invention has an HLB value, suitable for stabilizing an emulsion comprising the aqueous phase and the oil phase of the composition.

According to one or more embodiments of the present invention, the surface-active agent has a hydrophilic lipophilic balance (HLB) between about 9 and about 14 or more, which is the required HLB (the HLB required to stabilize an O/W emulsion of a given oil) of most oils and hydrophobic solvents. Thus, in one or more embodiments, the composition contains a single surface active agent having an HLB value between about 9 and 14 or more, and in one or more embodiments, the composition contains more than one surface active agent and the weighted average of their HLB values is between about 9 and about 14 or more In certain aspects, a sugar-based surfactant is present from about 1% w/w to about 20% w/w, preferably about 5% to about 15% w/w. In one aspect, the sugar-based surfactant is a sucrose ester having a hydrophilic and lipophilic balance (HLB) of between 5 to 16. In certain other aspects, the surfactant system has a HLB value of between 7 to 16 and preferably 15 or higher. The microemulsions of the present invention can have a mixture of sugar-based surfactants having differing HLB values, such as for example, 1 surfactant which has a value of 5 and another having a value of 16. All such combinations are within the scope of the present invention.

Suitable sucrose esters include sucrose myristate, sucrose laurate, sucrose oleate, sucrose palmitate, sucrose stearate or a combination thereof. Preferably, the sucrose ester is sucrose laurate. Those of skill in the art will know of other sucrose esters suitable for use in the present invention.

In certain aspects, a sugar surfactant is an alkyl polyglucoside. The alkyl polyglucosides are characterized by the length of the alkyl chain and the average number of glucose units linked to it i.e., the degree of polymerization (see, Rybinski et al., *Angew. Chem. Int.* Ed. 1998, 37, 1328-1345). The alkyl polyglucosides are commercially available from Akzo Nobel (Stenungsund, Sweden), BASF, Henkel (Düsseldorf, Germany), ICI (Middlesborough, U.K.), SEPPIC, and Union Carbide (Danbury, USA). Suitable alkyl polyglucosides include, but are not limited to, a $C_{8-16}$ decyl glucoside, a $C_{8-16}$ coco glucoside, a $C_{12-16}$ lauryl glucoside or a combination thereof. For the avoidance of doubt, the alkyl polyglucoside molecule consists of an alkyl functional group, e.g., "decyl," attached to a carbon chain distribution (e.g., polydisperse) of polyglucoside units, e.g., "$C_{8-16}$" or a degree of polymerization of between 8 to 16 glucose units. In a preferred aspect, the alkyl polyglucoside is present from about 1% w/w to about 5% w/w.

In certain aspects, the microemulsions of the present invention comprise a co-surfactant. The preferred co-surfactants used in the composition are considered as GRAS (Generally Recognized As Safe) by FDA. Suitable co-surfactants include, but are not no limited to, a polyhydric alcohol such as for example, a dihydric alcohol, a trihydric alcohol or a sugar alcohol. In certain aspects, the microemulsion of the present invention contains a polyhydric alcohol in an amount of from about 1% w/w to about 10% w/w.

In one preferred aspect, the dihydric alcohol is a glycol. Suitable glycols include, but are not limited to, ethylene glycol, propylene glycol or a combination thereof. In a preferred aspect, the co-surfactant is propylene glycol. In other aspects, the microemulsion of the present invention comprises a trihydric alcohol, such as glycerol.

In certain other aspects, the microemulsion of the present invention comprises a sugar alcohol. Suitable sugar alcohols include, but are not limited to, sorbitol, manitol, xylitol or a combination thereof.

In certain embodiments, the present invention provides microemulsions comprising an essential oil, a pharmaceutically acceptable oil, or a combination thereof. In one aspect, the oil is present in an amount from about 0.5% w/w to about 10% w/w.

Preferably, the essential oil is derived from a plant extract. Non-limiting examples of oils suitable for use in the microemulsion of the present invention include, but are not limited to, eucalyptus oil, lavender oil, tea tree oil, green tea oil, rosemary oil, patchouli oil, cedar wood atlas oil, clove leaf oil, palmarosa oil, grapefruit oil, bergamot calabrian oil, pine oil, cardamom oil, peppermint oil, cinnamon leaf oil, and ylang ylang oil or a mixture thereof. In certain aspects, the oil phases used in present invention include natural essential oils normally extracted from various parts of plants by steam distillation.

In one aspect, the microemulsions of the present invention further comprise a vitamin. In certain preferred aspects, poorly water-soluble vitamins such as vitamin A, E, and K and their derivatives are especially suitable for the present invention. In one aspect, the vitamin is present in an amount of 0.01% w/w to about 5% w/w.

In another aspect, the microemulsions of the present invention comprise an antioxidant or radical scavenger useful in context of the present invention include ascorbic acid (vitamin C) and its salts, tocopherol (vitamin E), and its derivatives such as tocopherol sorbate, other esters of tocopherol, butylated hydroxy benzoic acids and their salts, 6-hydroxy-2,5,7,8-tetramethylchroman-2-carboxylic acid, gallic acid and its alkyl esters, especially propyl gallate, uric acid and its salts and alkyl esters, sorbic acid and its salts, the ascorbyl esters of fatty acids, amines (e.g., N,N-diethylhydroxylamine, amino-guanidine), sulfhydryl compounds (e.g., glutathione), and dihydroxy fumaric acid and its salts may be used, as well as EDTA, BHT and the like.

In certain embodiments, the present invention provides microemulsions further comprising a thickening agent. Suitable thickeners include for example, xanthan gum, hydroxyethylcellulose, carrageenan or a combination thereof. In one aspect, the thickener is present in an amount of, for example, 0.01% w/w to about 5% w/w. In other aspects, the thickener may be employed in amount of 0.1 to 5% w/w by weight for improving the desired viscosity for topical use.

Preferably, the thickening agent is substantially chemically inert to other ingredients. The thickening agent can be synthetic or naturally occurring. In some embodiments, the thickening agent is a hydrocolloid, for example, agar, alginate, arabinoxylan, carrageenan, carboxymethylcellulose, hydroxypropyl methylcellulose, cellulose, curdlan, gelatin, gellan, β-glucan, guar gum, gum arabic, locust bean gum, pectin, starch, carbomers, or xanthan gum. In some embodiments, the thickening agent is a natural gum, for example, gum arabic, tragacanth gum, xanthan gum, carrageenan (alginate gum), pectin or guar gum. In some embodiments, the thickening agent is xanthan gum.

In certain preferred aspects, the microemulsions described herein are substantially free of an alkanol. As used herein, "substantially free of an alkanol" refers to less than about 2.0% or about 0%.

In certain aspects, a microemulsion of the present invention, with or without further active ingredients, is suitable for the further application as a "cosmeceutical" preparation (cosmetic products with therapeutic benefit), to treat "cosmetic" skin disorders, such as aging skin, wrinkles, hyperpigmentation (melasma, chloasma, freckles, and the like), scaly skin and other skin undesirable properties.

In certain aspects, the term "cosmetic active agent" refers to the principle component or components that at to perform the primary function or functions of the cosmetic composition. Any cosmetic active agent is considered an "active agent" in the context of the present invention. The CTFA Cosmetic Ingredient Handbook describes a wide variety of non-limiting cosmetic active agents commonly used in the skin care industry, which are suitable for use in the compositions of the present invention. Examples of these ingredient classes include: abrasives, absorbents, aesthetic components such as fragrances, pigments, colorings/colorants, essential oils, astringents, clove oil, menthol, camphor, eucalyptus oil, eugenol, menthyl lactate, witch hazel distillate, anti-acne agents, antimicrobial agents (e.g., iodopropyl butylcarbamate), antioxidants, biological additives, cosmetic astringents, cosmetic biocides, reducing agents, sequestrants, skin bleaching and lightening agents (e.g., hydroquinone, kojic acid, ascorbic acid, magnesium ascorbyl phosphate, ascorbyl glucosamine), skin-conditioning agents (e.g., humectants, including miscellaneous and occlusive), skin soothing and/or healing agents (e.g., panthenol and derivatives (e.g., ethyl panthenol), aloe vera, pantothenic acid and its derivatives, allantoin, bisabolol, and dipotassium glycyrrhizinate), and vitamins and derivatives thereof.

In certain other embodiments, the microemulsion of the present invention further comprises an active agent. Suitable active agents include, but are not limited to, an antibacterial, an antibiotic, an antifungal, a retinoid, an insecticide or a combination thereof.

In certain preferred aspects, the antibacterials include, but are not limited to, chloramphenicol, synthetic and semi-synthetic penicillins, beta-lactams, quinolones, fluoroquinolnes, macrolide antibiotics, azelaic acid, silicylates, peptide antibacterials, cyclosporines or a combination thereof.

In certain other aspects, the antibiotics include, but are not limited to, clindamycin, erythromycin, tetracycline, minocycline, doxycycline, pharmaceutically acceptable salts thereof, or prodrugs thereof.

In certain preferred aspects, the antifungal agents include, but are not limited to, clotrimazole, miconazole, metronidazole, ketoconazole, econazole, butoconazole, oxiconazole or sulconazole.

In certain other embodiments, the retinoids include, but are not limited to, vitamin A, retinol (cis or trans), retinal (cis or trans), retinoic acid (cis), tretinoin, hydroxyretroretinol, didehydroretinoic acid, etretinate, retinyl palmitate, β-carotene, tazarotene, acitretin, adapalene or a combination thereof.

In certain preferred aspects, the insecticide is a natural insecticide.

In certain other embodiments, the microemulsions are suitable for delivering skin protecting and revitalizing antioxidants such as polyunsaturated fatty acids containing omega-3 and omega-6 fatty acids (e.g., linoleic and linolenic acid, gamma-linoleic acid (GLA), eicosapentaenoic acid (EPA) and docosahexaenoic acid (DHA)), which are beneficial in the treatment of psoriasis and other skin inflammation conditions. Likewise, emollients and silicone oils exert moisture-retaining and skin protective effects on the skin. Thus, a skin protective composition is provided, wherein the hydrophobic solvent comprises in full or in part, a solvent, selected from the group of emollients, silicone oil and oils, rich in unsaturated fatty acids, thus, affording a synergistic therapeutic effect of the anti-oxidants scavenger agent and the vehicle components.

III. Preparation

In another embodiment, the present invention further provides methods for making the microemulsion described herein. The present invention provides a method for making a microemulsion for a topical application, the method comprising:

(a) admixing a surfactant and optionally a co-surfactant with an essential oil to form an oil phase;
(b) adding the oil phase to water to form a coarse macroemulsion; and
(c) shaking or stirring the coarse macroemulsion to spontaneously form the microemulsion.

In this embodiment, the method includes admixing a surfactant and optionally a co-surfactant with an essential oil to from an oil phase. Preferably, the oil is added to the surfactant mixture under continuous gentle stirring. In this aspect, the oil phase in the formulation is dispersed in the continuous aqueous phase. Preferably, double-filtered (0.45 µm, Millipore) deionized water is used as the water phase. The mixture of surfactant and oil is added to the water phase until a clear one phase solution changes to an opaque mixture (i.e. coarse macroemulsion) indicating two or more phases. The stable microemulsion forms spontaneously and an equilibrium is reached within a short time by gentle hand shaking or stirring. Thereafter, each phase solution can then be examined by optical microscope and/or under cross-polarized light to determine if it is isotropic or a liquid crystalline phase. It can be operated with polarizations placed in the crossed position, e.g., plane polarization with one transmitter-receiver pair being "vertically polarized" and the other pair being "horizontally polarized" which then produces the darkest matrix appearance.

Turning now to FIG. 1, as shown therein, the microemulsions of the present invention provide a pseudoternary phase diagram. In this aspect, the microemulsion contains sucrose monolaurate, essential oils and deionized water. The stable microemulsion domain appears in the shaded area ("ME") above the upper boundary curves (e.g., eucalyptus oil-based microemulsion) on a weight basis. In one aspect, this shaded area represents preferred weight percentages of components of the invention.

Figure 2:
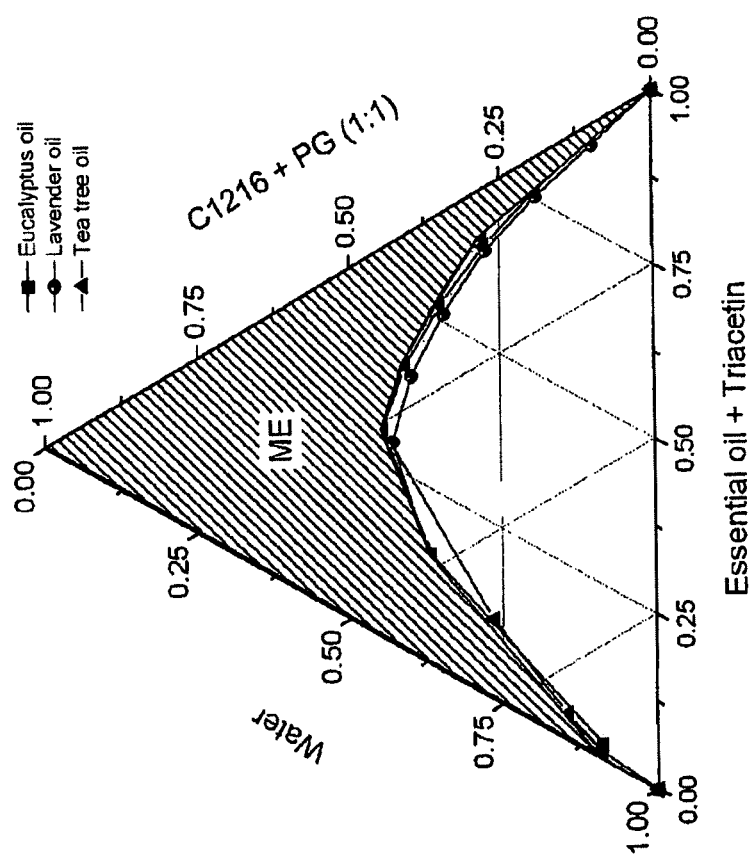
FIG. 2 shows a pseudoternary phase diagram of a microemulsion containing triacetin illustrating a stable microemulsion domain.

Similarly, turning to FIG. 2, a pseudoternary phase diagram illustrates a microemulsion containing sucrose monolaurate, mixtures of essential oils and triacetin as the oil phase and deionized water as the aqueous phase. The stable microemulsion domain appears in the shaded area ("ME") above the upper boundary curves (e.g., eucalyptus oil-based microemulsion) on a weight basis. In one aspect, this shaded area represents preferred weight percentages of components of the invention.

In certain embodiments, the present invention can be applied as a topical delivery system to the surface of skin as a cream, gel, or spray form in cosmetic and pharmaceutical applications with good biological compatibility. The present invention can also be used as skin antioxidant to reduce the free radicals causing skin aging and disease and antimicrobial agent(s) to inhibit the growth of various infectious pathogens.

In certain instances, the microemulsions contain a pH-adjusting agent, for example, an acid, a base, a buffering pair or a buffering agent. In some embodiments, the pH-adjusting agent is a buffering agent, for example, a buffering pair to stably maintain a desired pH. The chosen buffering agent or buffering pair selected will depend on the active ingredients included. An appropriate buffer will have a pKa value that is at or near the desired pH. The pH of the microemulsion will depend on the active agents included in the formulations. The final pH will promote the chemical and physical stability of the active agents.

IV. Uses

In still yet another embodiment, the present invention provides a use of a microemulsion, comprising:
(a) up to 20% w/w of a sugar-based surfactant selected from the group of a sucrose ester, an alkyl polyglucoside and a combination thereof;
(b) up to 10% w/w of a polyhydric alcohol;
(c) up to 10% w/w of an oil selected from the group of an essential oil, a pharmaceutically acceptable oil, and combinations thereof; and
(d) up to 95% w/w water in the manufacture of a medicament for a topical application treatment.

In certain embodiments, the microemulsion further comprises an active agent such as an antibacterial, an antibiotic, an antifungal, a retinoid, an insecticide and a combination thereof.

In certain embodiments, the microemulsions are useful in the treatment of acne, wrinkles and scars. Examples of useful anti-acne actives include resorcinol, sulfur, salicylic acid and salicylates, alpha-hydroxy acids, nonsteroidal anti-inflammatory agents, benzoyl peroxide, retinoic acid, isoretinoic acid and other retinoid compounds, adapalene, tazarotene, azelaic acid and azelaic acid derivatives, antibiotic agents, such as erythromycin and clyndamycin, zinc salts and complexes, and combinations thereof, in a therapeutically effective concentration.

In certain embodiments, the microemulsions are useful vehicles for anti-wrinkle/anti-atrophy active agents such as sulfur-containing D and L amino acids and their derivatives and salts, particularly the N-acetyl derivatives; thiols; hydroxy acids (e.g., alpha-hydroxy acids such as lactic acid and glycolic acid and their derivatives and salts; or beta-hydroxy acids such as salicylic acid and salicylic acid salts and derivatives), urea, hyaluronic acid, phytic acid, lipoic acid; lysophosphatidic acid, skin peel agents (e.g., phenol, resorcinol and the like), vitamin B3 compounds (e.g., niacinamide, nicotinic acid and nicotinic acid salts and esters, including non-vasodilating esters of nicotinic acid (such as tocopheryl nicotinate), nicotinyl amino acids, nicotinyl alcohol esters of carboxylic acids, nicotinic acid N-oxide and niacinamide N-oxide), vitamin B5 and retinoids (e.g., retinol, retinal, retinoic acid, retinyl acetate, retinyl palmitate, retinyl ascorbate). In the case of dry, scaly skin (xerosis) and ichthyosis such agents can alleviate the symptoms by temporary relief of itching associated with these conditions.

The invention also provides for methods of therapeutically and prophylactically treating a dermatological condition by topically applying the microemulsion of the invention to affected areas. Exemplified dermatological conditions suitable for treatment by the present invention include rashes, eczema, contact dermatitis, acne (including acne vulgaris and acne rosacea), fungal infections, bacterial infections, and the like.

Acne is treated both therapeutically and prophylactically by applying the microemulsion to the skin in areas where acne lesions are present or likely to be present. The microemulsion is generally rubbed into the skin until the microemulsion is partially or totally absorbed and or adsorbed. The microemulsion can be applied one, two, three, four or more times a day, as needed, or as directed by a healthcare provider.

V. Examples

The following examples further illustrate the present invention.

Example 1 illustrates several alkanol-free microemulsion formulations containing pure essential oils as the oil phase.

| Ingredients | Percent by Weight | | | | |
|---|---|---|---|---|---|
| C1216* | 14% | 8% | 8% | 4% | 4% |
| Propylene glycol | 14% | 8% | 8% | 4% | 4% |
| *Eucalyptus* oil | 7% | — | — | — | — |
| Green tea oil | — | 4% | — | — | — |
| *Cardamom* oil | — | — | 4% | — | — |
| Rosemary oil | — | — | — | 2% | — |
| Patchouli oil | — | — | — | — | 2% |
| Water | to 100% | | | | |

*C1216 is a trademark of sucrose monolaurate (RYOTO ®, commercially available from Mitsubishi-Kagaku Co.) having a hydrophilic and lipophilic balance (HLB) = 16.

Example 2 illustrates several alkanol-free microemulsion formulations with a mixture of essential oils and pharmaceutically acceptable oil as the oil phase.

| Ingredients | Percent by Weight | | | |
|---|---|---|---|---|
| C1216 | 8.5% | 6.0% | 9.0% | 4.0% |
| Propylene glycol | 8.5% | 6.0% | 9.0% | 4.0% |
| Clay sage oil | 1.5% | — | — | — |
| *Eucalyptus* oil | — | 1.5% | — | — |
| Lavender oil | — | — | 1.0% | — |
| Tea tree oil | — | — | — | 1.0% |
| Triacetin | 1.5% | 1.5% | 1.0% | 1.0% |
| Water | to 100% | | | |

Figure 3:
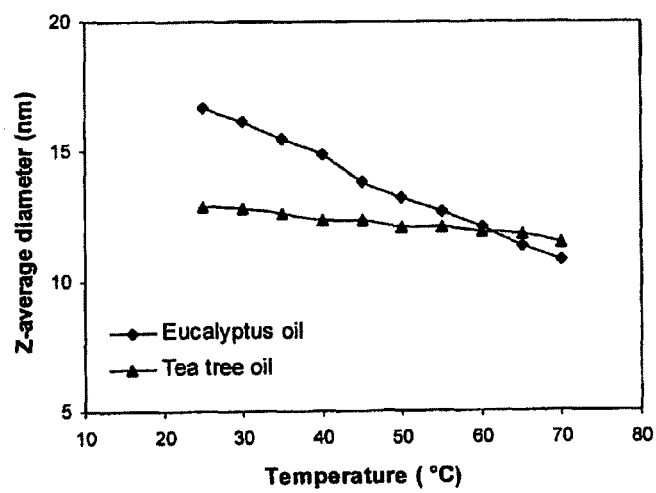
FIG. 3 shows a Z-average particle size of an oil-in-water microemulsion at a temperature in the range of from 25° C. to 70° C.

As shown in FIG. 3, the Z-average particle size of an oil-in-water microemulsion containing sucrose monolaurate, mixtures of essential oils and triacetin as oil phase and deionized water as aqueous phase at a temperature in the range of from 25 to 70° C. Advantageously, the droplet size of these formulations was less sensitive to change in temperature.

Example 3 illustrates a microemulsions with poorly water-soluble vitamins as an antioxidant agents.

| Ingredients | Percent by Weight | | | | | |
|---|---|---|---|---|---|---|
| Sucrose laurate | 9.0% | 9.0% | 8.0% | 9.0% | 9.0% | 8.0% |
| Propylene glycol | 9.0% | 9.0% | 8.0% | 9.0% | 9.0% | 8.0% |
| *Eucalyptus* oil | 0.5% | 0.5% | 1.0% | — | — | — |
| Tea tree oil | — | — | — | 0.5% | 0.5% | 1.0% |
| Triacetin | 0.5% | 0.5% | 1.0% | 0.5% | 0.5% | 1.0% |
| Vitamin E | 0.1% | — | 0.01% | 0.01% | — | 0.01% |
| Vitamin E acetate | — | 0.1% | — | — | 0.1% | — |
| Water | to 100% | | | | | |

The physical stability of the invented microemulsions mentioned in examples 1, 2 and 3 were also examined by centrifuge test at 5000×g for 30 minutes and freeze-thaw test at different storage temperatures (5 to 70° C.) for 24 hours. All tested microemulsions were temperature-insensitive up to 70° C. and stable more than 6 months at room temperature without any phase change and/or phase separation.

All publications and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. An oil-in-water microemulsion for a cosmetic or a pharmaceutical application, said microemulsion comprising:
   (a) 1% to 20% w/w of surfactant system comprising sucrose laurate;
   (b) 1% to 10% w/w of propylene glycol;
   (c) 0.5% to 10% w/w of an essential oil selected from the group consisting of eucalyptus oil, lavender oil, tea tree oil, green tea oil, rosemary oil, patchouli oil, cedar wood atlas oil, clove leaf oil, palmarosa oil, grapefruit oil, bergamot calabrian oil, pine oil, cardamom oil, clary sage oil, peppermint oil, cinnamon leaf oil, ylang ylang oil, and a combination thereof;
   (d) triacetin; and
   (e) water,
wherein the microemulsion includes less than 2% w/w of a monohydric alkanol; and wherein the microemulsion is suitable for topical application.

2. The microemulsion of claim 1, wherein said surfactant system further comprises a C12-16 lauryl glucoside; and wherein the combination of the C12-16 lauryl glucoside and sucrose laurate is up to 20% w/w.

3. The microemulsion of claim 1, wherein said C12-16 lauryl glucoside is present from about 1% w/w to about 5% w/w.

4. The microemulsion of claim 1, wherein said microemulsion comprises from 0.5 to 1.5% w/w triacetin.

5. The microemulsion of claim 4, wherein said essential oil is a member selected from the group consisting of eucalyptus oil, lavender oil, tea tree oil, green tea oil, rosemary oil, patchouli oil, cardamom oil, clary sage oil, and a combination thereof.

6. The microemulsion of claim 1, wherein said microemulsion further comprises a vitamin.

7. The microemulsion of claim 6, wherein said vitamin is present in an amount of 0.01% w/w to about 5% w/w.

8. The microemulsion of claim 6, wherein said vitamin is a member selected from the group consisting of vitamin A, vitamin E, vitamin K, a derivative thereof and a combination thereof.

9. The microemulsion of claim 1, wherein said microemulsion further comprises a thickening agent.

10. The microemulsion of claim 9, wherein said thickener is present in an amount of 0.01% w/w to about 5% w/w.

11. The microemulsion of claim 9, wherein said thickener is a member selected from the group consisting of xanthan gum, hydroxyethylcellulose, carrageenan and a combination thereof.

12. The microemulsion of claim 1, wherein said microemulsion further comprises an active agent.

* * * * *